United States Patent
Liao et al.

(10) Patent No.: US 9,855,441 B2
(45) Date of Patent: *Jan. 2, 2018

(54) METHOD FOR PRODUCING MICRO PLASMA WITH BIOCOMPATIBILITY

(71) Applicant: National Cheng Kung University, Tainan (TW)

(72) Inventors: Jiunn-Der Liao, Tainan (TW); Pei-Lin Shao, Tainan (TW)

(73) Assignee: NATIONAL CHENG KUNG UNIVERSITY, Taiwan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/067,235

(22) Filed: Mar. 11, 2016

(65) Prior Publication Data

US 2016/0250493 A1 Sep. 1, 2016

Related U.S. Application Data

(63) Continuation of application No. 14/230,133, filed on Mar. 31, 2014, now Pat. No. 9,318,305.

(51) Int. Cl.
*A61M 37/00* (2006.01)
*A61N 1/44* (2006.01)
*H01J 37/32* (2006.01)

(52) U.S. Cl.
CPC .............. *A61N 1/44* (2013.01); *A61M 37/00* (2013.01); *H01J 37/32449* (2013.01); *H01J 37/32981* (2013.01); *H05H 2245/122* (2013.01)

(58) Field of Classification Search
CPC ....................................................... A61N 1/44
USPC .......... 604/19, 23; 422/906; 250/428, 432 R, 250/435; 315/111.11, 111.21
See application file for complete search history.

(56) References Cited

U.S. PATENT DOCUMENTS

| | | | |
|---|---|---|---|
| 7,608,839 B2 * | 10/2009 | Coulombe | H05H 1/24 250/423 F |
| 8,764,701 B1 * | 7/2014 | Hicks | A61B 18/042 315/111.21 |
| 2008/0125742 A1 * | 5/2008 | Podhajsky | A61M 35/00 604/500 |
| 2012/0063966 A1 * | 3/2012 | Liao | A61L 2/14 422/186 |
| 2012/0086339 A1 * | 4/2012 | Lloyd | A61C 17/02 315/111.21 |

FOREIGN PATENT DOCUMENTS

| | | |
|---|---|---|
| CN | 102404927 A | 4/2012 |
| TW | 201210640 A | 3/2012 |

OTHER PUBLICATIONS

Ngo et al., "Increased Fibroblast Cell Proliferation and Migration Using Atmospheric N2/Ar Micro-Plasma for the Stimulated Release of Fibroblast Growth Factor-7", vol. 11, Issue 1, pp. 80-88, Jan. 2014.

* cited by examiner

*Primary Examiner* — Thuy Vinh Tran
(74) *Attorney, Agent, or Firm* — Bacon & Thomas, PLLC

(57) ABSTRACT

The object of the present invention is to provide a method for producing a micro-plasma with biocompatibility. The produced micro-plasma is a low temperature, adjustable micro-plasma with low energy consumption. The method provides a device comprising a first gas storage unit, a second gas storage unit, a unit for producing the micro-plasma, and a power supply unit.

15 Claims, 19 Drawing Sheets

METHOD FOR PRODUCING MICRO PLASMA WITH BIOCOMPATIBILITY

CROSS REFERENCE TO RELATED APPLICATION

This application is a continuation application of U.S. patent application Ser. No. 14/230,133, filed on Mar. 31, 2014, which is now U.S. Pat. No. 9,318,305 issued on Apr. 19, 2016, the subject matter of which is incorporated herein by reference.

BACKGROUND OF THE INVENTION

1. Field of the Invention

The present invention relates to a method for producing micro-plasma with biocompatibility, and more particularly, to a low temperature, adjustable micro-plasma with low energy consumption.

2. Description of Related Art

Micro-plasma refers to a reactive state in which gases are partially dissociated by the application of energy, to generate heat, light, charged particles, neutral active species, etc. Currently, micro-plasma technology for skin tissue applications is limited to thermal effects produced by the energy of plasma.

Almost everyone has been subjected to wounding due to trauma on skin in daily life. In 24 to 48 hours after formation of wounds, coagulation and inflammation are the first phase, and then cell proliferation phase lasts for 2-10 days; and finally, remodeling phase progresses for 1 to 12 months.

Since the thermal effect of laser will make skin temporarily dehydrated, hydropenia, the most important postoperative course would care, is to preserve moisture and apply sun-proof clothing such as masks or dressing etc., to promote repair of damaged tissue. It will take about 4-12 weeks to recover wounds caused by invasive laser vaporization to a normal state; however, the longer the period of wound healing, the higher the probability that the postoperative complication such as pigmentation after infection and inflammation will occur.

Moreover, masks or dressings used during wound healing contain antimicrobial or antibiotic ingredients, and excessive use of antibiotics is detrimental, rather than conducive to wound healing. So far, there is no standard data to regulate the appropriate dose of antibiotics and sun-proof ingredients after a skin laser treatment. The published scientific journals disclosed that after the skin receives a laser treatment, the applied antibiotics and sun-proof ingredients may easily reside in the wounds due to the incompleteness of the skin, thereby causing sensitive skin and even toxicity phenomenon due to excessive absorption.

The effect of skin laser surgery often fails to comply with the patient's expectation, and thus how to achieve the optimal effect after surgery and minimal damage, has always been the ultimate goal of medical care. In recent years, the issue relating to wounds recovery and tissue regeneration draws attention of global research and development teams, and the applications of micro-plasma medicine on healing of infectious wound or improvement of dressing material has become the hottest topic. It is an ultimate aim of medical care to achieve skin repair after laser surgery with optimal effect, minimal damage and reduced complication.

Therefore, there is an urgent need for a method or system with low-temperature, no accumulation of thermal effect, to shorten the recovery time of sensitive wounds after laser therapy.

SUMMARY OF THE INVENTION

An object of the present invention is to provide a method for producing micro-plasma with biocompatibility, to produce a micro-plasma with low temperature, adjustable plasma composition, and low energy consumption so as to reduce damage caused by the thermal effect accumulated on skins.

To achieve above object, the present invention is to provide a method for producing a micro-plasma with biocompatibility, comprising the following steps: (A) providing a device comprising a first gas storage unit, a second gas storage unit, a micro-plasma generation unit, and a power supply unit; (B) introducing helium or argon stored in the first gas storage unit, into the micro-plasma generation unit to excite a micro-plasma to a steady state within a predetermined time; and (C) introducing oxygen or nitrogen stored in the second gas storage unit, into the micro-plasma generation unit so as to produce micro-plasma excited species. By this method, a small breakdown voltage is produced, and since the micro-plasma is excited with a low power and low breakdown voltage, the average temperature of micro-plasma can be reduced.

The micro-plasma generation unit in the step (A) of the present invention may further comprise a capillary tube in which the micro-plasma is excited to produce a low temperature micro-plasma.

The excitation power of the micro-plasma in the present invention is preferably 1-50 W.

In the step (B) of the present invention, a flow rate of helium or argon stored in the first gas storage unit is preferably 1-10 slm, and more preferably 1-5 slm.

In the step (C) of the present invention, the addition ratio of oxygen stored in the second gas storage unit is preferably 0.1-5%, and more preferably 0.1-2%.

In the step (C) of the present invention, the addition ratio of nitrogen stored in the second gas storage unit is preferably 0.1-2%, and more preferably 0.1-1%.

The processing time of the micro-plasma according to the present invention is 5-300 seconds.

The step (C) of the present invention may further comprise setting a working distance, which is a distance between a subject and the micro-plasma generation unit, and the working distance is preferably 1-12 mm.

The method of the present invention may further comprise an operation power of preferably 15-30 W, and more preferably 17-25 W.

The device of the step (A) according to the present invention may further comprise a temperature measurement system for measuring the average temperature of the micro-plasma, which is in a range of 34-40° C.

The device of the step (A) according to the present invention may further comprise a micro-plasma emission spectrometer for quantitatively or qualitatively detecting the type of the micro-plasma excited species, and the micro-plasma excited species may be reactive oxygen species (ROS) or reactive nitrogen species (RNS).

The effect of the present invention is to reduce the temperature of the micro-plasma. When the low temperature micro-plasma is applied on the skin, the skin may not feel burning even after treatment with the micro-plasma for a long time, and the sensitive skin after the laser treatment may be subjected to a gentle skin care. In addition, the energy required for maintaining the micro-plasma is significantly reduced by separately introducing the reactive gases and the micro-plasma excitation gases, which may result in a very low energy consumption. In summary, the present invention is characterized by providing a method for producing a micro-plasma at low temperature with adjustable plasma composition, and low energy consumption, as well as a device for producing micro-plasma and the application of the related parameters as above.

DETAILED DESCRIPTION OF THE PREFERRED EMBODIMENT

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention, and those skilled in the art will appreciate that various modifications, additions and substitutions are possible.

As used herein, the term "low temperature" refers to the meaning used in the biomedical field. For human skin tissue, according to human skin physiology, central body of homoeothermic has a temperature of $37.0 \pm 2°$ C. to maintain the normal physiological functions. When the temperature is over 43° C. or below 24-25° C., organisms may be subjected to irreversible pathological changes. As in static activity with thin clothing at 27-29° C., the comfortable body surface temperature for skin is 31-34° C., and the cold receptors distributed in the dermal layer will be activated at 7-40° C., while the warmth receptors will be activated at 30-50° C.

As used herein, the term "the low temperature micro-plasma" refers to a micro-plasma having an average temperature of 31-34° C., which is suited for use on human skins, and does not create uncomfortable feeling to the human body. The uncomfortable feeling refers to a pain feeling resulted from activating the pain receptors by overheating or overcooling. When wounds are present on the skin, the temperature of the site of the wound may reach over $37.0 \pm 2°$ C. due to inflammatory reaction. Therefore, the output temperature of the device according to the present invention generally falls within the above range of temperature. In addition, the low temperature, non-thermal micro-plasma typically has a temperature of below 100° C.

In the present invention, the steady state of the micro-plasma is defined as that the micro-plasma plume radiate steadily without twinkle, and the gas flow controller shows a steady value. It may require 10 to 15 seconds to reach the steady state.

Example 1

Figure 1:
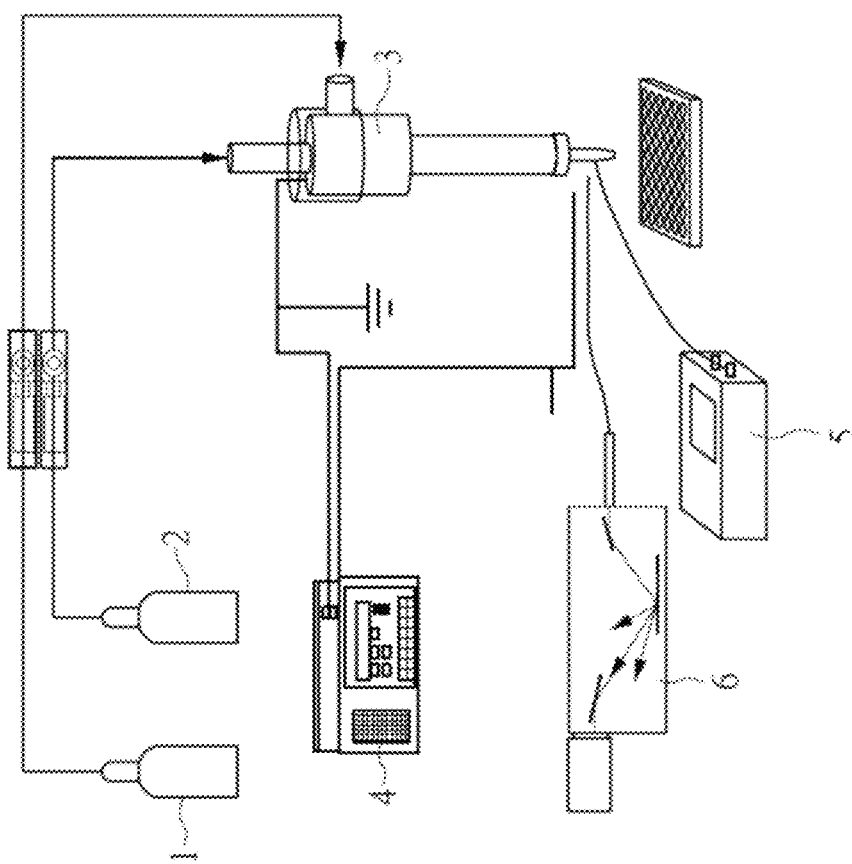
FIG. 1 illustrates a schematic view of the device of the present invention.

The Example 1 of the present invention is to provide a method for producing micro-plasma with biocompatibility, and the method comprises the following steps: providing a device comprising a first gas storage unit 1, a second gas storage unit 2, a micro-plasma generation unit 3, and a power supply unit 4, as shown in FIG. 1. The first gas stored in the first gas storage unit 1 was introduced into the micro-plasma generation unit 3, and then the micro-plasma was excited from the first gas and reached a steady state after 10 to 15 seconds, wherein the first gas was argon. Then the second gas stored in the second gas storage unit 2 was introduced into the micro-plasma generation unit 3 to produce the micro-plasma excited species. Finally, the type of the micro-plasma excited species was identified according to the emission spectrum measured by the micro-plasma emission spectrometer 6.

The second gas of Example 1 was nitrogen, and the addition ratio thereof was 0%, 0.1%, 0.5%, and 2%. The excitation power of the micro-plasma was 15, 16, 17, 18, 19, 20, and 25 W.

Figure 2:
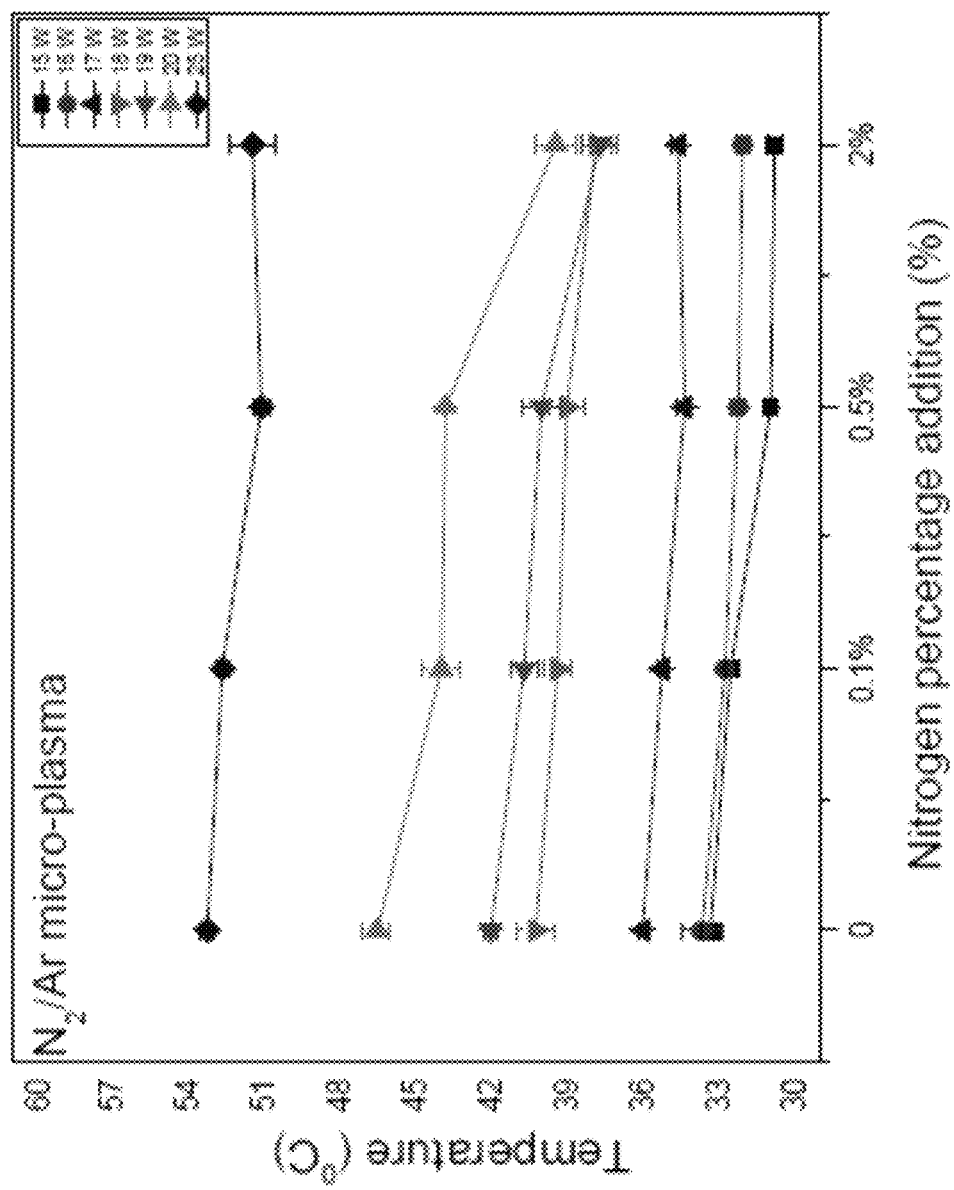
FIG. 2 is a diagram showing the relationship between the addition ratio of nitrogen and temperature of different excitation powers of the micro-plasma according to Example 1 of the present invention.

FIG. 2 is a diagram showing the relationship between the addition ratio of nitrogen and temperature in the conditions of Example 1. FIG. 2 is a diagram showing the relationship between the addition ratio of nitrogen (0%, 0.1%, 0.5%, and 2%) and temperature of different excitation powers of the micro-plasma (15, 16, 17, 18, 19, 20, and 25 W). The result of FIG. 2 indicates that by using an excitation power of lower than 25 W, the produced plasma of Example 1 is in a temperature range between 35 to 54° C., that is, a low temperature micro-plasma between 31 to 34° C. can be achieved.

Example 2

In Example 2, the steps were substantially the same as in Example 1, except for the set conditions of the second gas. The second gas of Example 2 was oxygen, and the addition ratio of the oxygen was 0%, 0.1%, 0.5%, and 2%.

Figure 3:
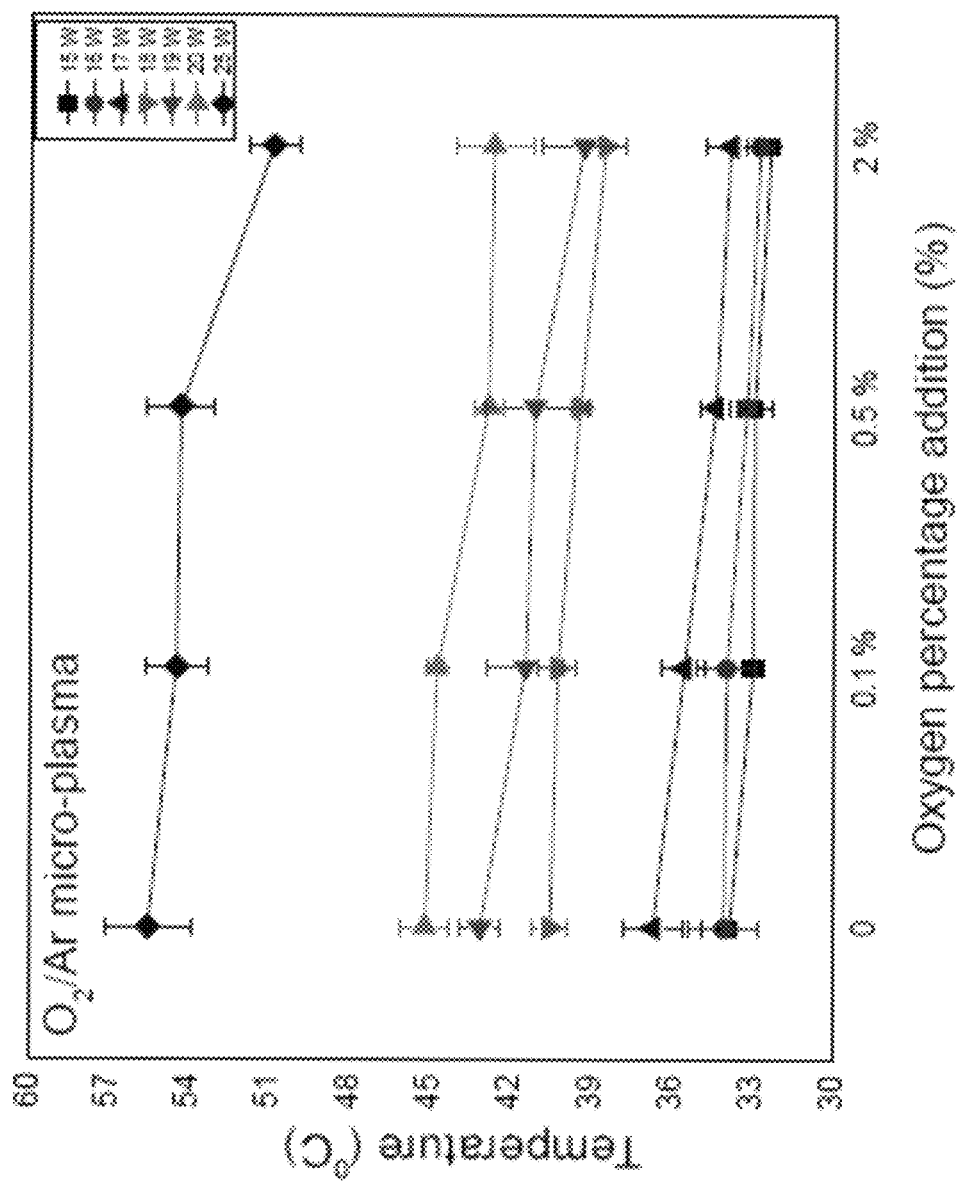
FIG. 3 is a diagram showing the relationship between the addition ratio of oxygen and temperature of different the excitation powers of the micro-plasma according to Example 2 of the present invention.
Figure 4:
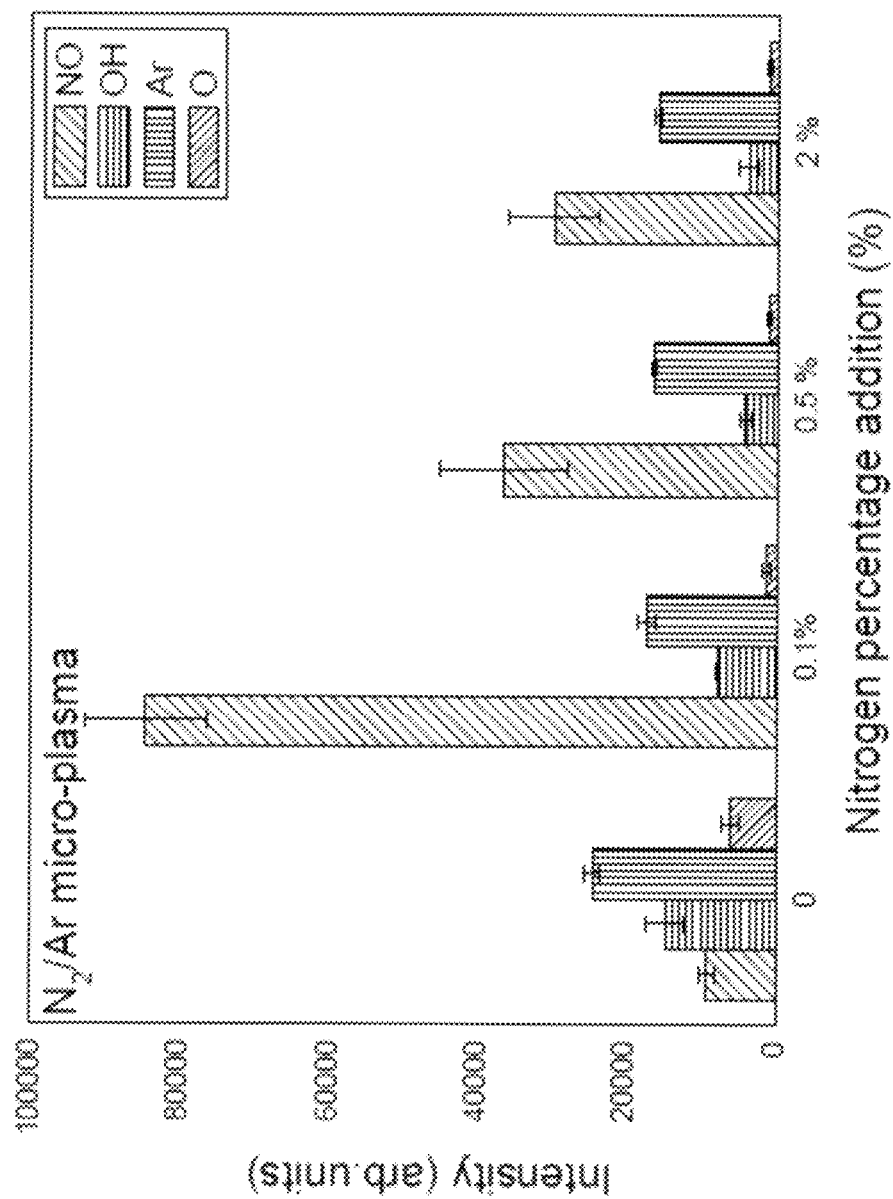
FIG. 4 is a diagram showing the relationship between the intensity of the produced micro-plasma excited species and the addition ratio of nitrogen according to Example 2 of the present invention.

FIG. 3 is a diagram showing the relationship between the addition ratio of oxygen and temperature in the conditions of Example 2. The result of FIG. 3 indicates that the low temperature micro-plasmas required by the present invention may be produced by adjusting the addition ratio of oxygen and excitation power. FIG. 3 is a diagram showing the relationship between the addition ratio of oxygen (0%, 0.1%, 0.5%, and 2%) and temperature of different excitation powers of the micro-plasma (15, 16, 17, 18, 19, 20, and 25 W). FIG. 4 is a diagram showing the relationship between the intensity of the produced micro-plasma excited species and the addition ratio of nitrogen, wherein in the condition of Example 1, the excited species were NO, OH, Ar and O. The result of FIG. 4 indicates that the exciting species with different intensities may be produced by varying the addition ratio of nitrogen, and therefore, the micro-plasma is adjustable.

Figure 5:
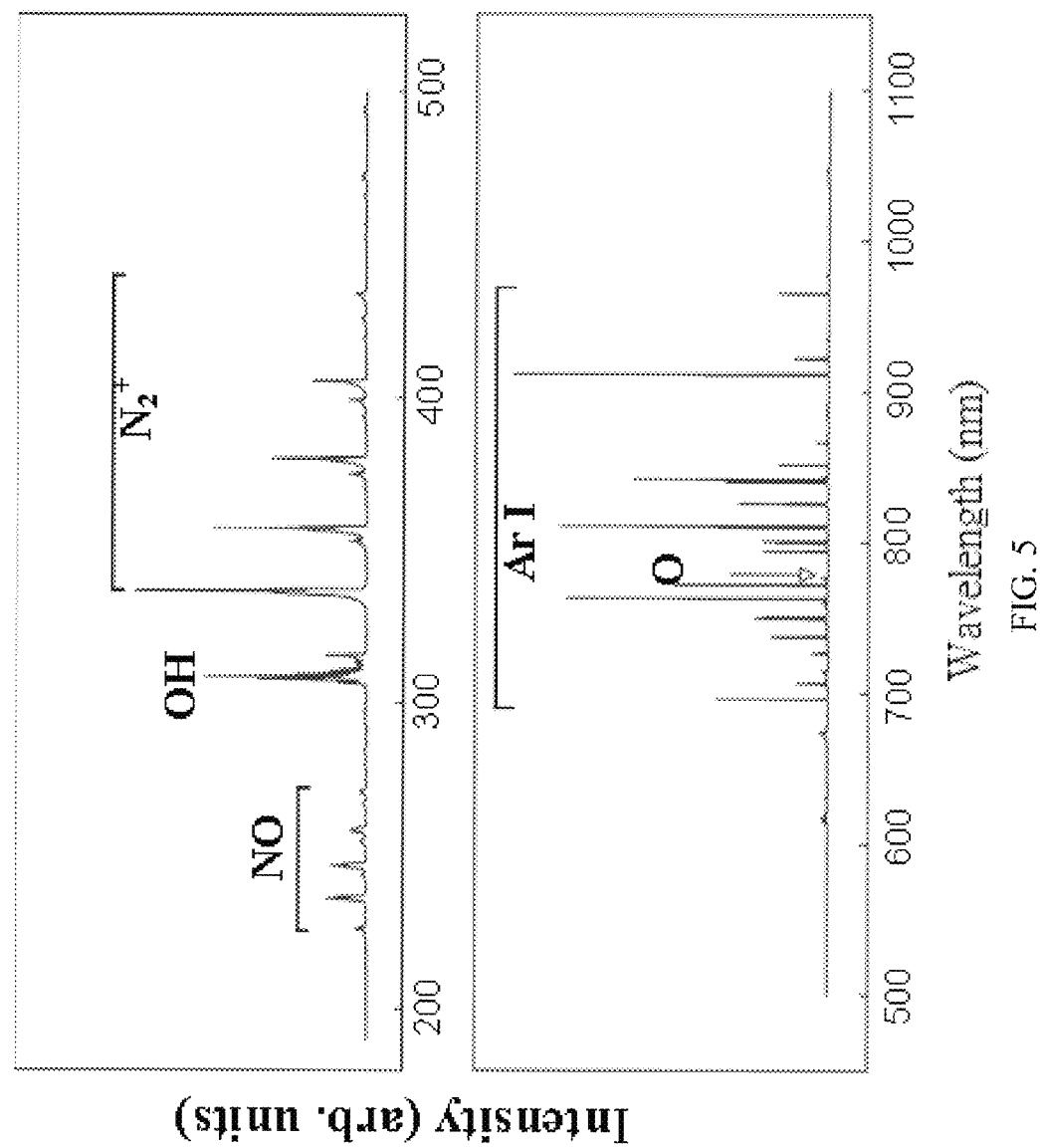
FIG. 5 shows the emission spectra of the major micro-plasma excited species at 190-550 and 550-1000 nm according to Example 2 of the present invention.
Figure 6:
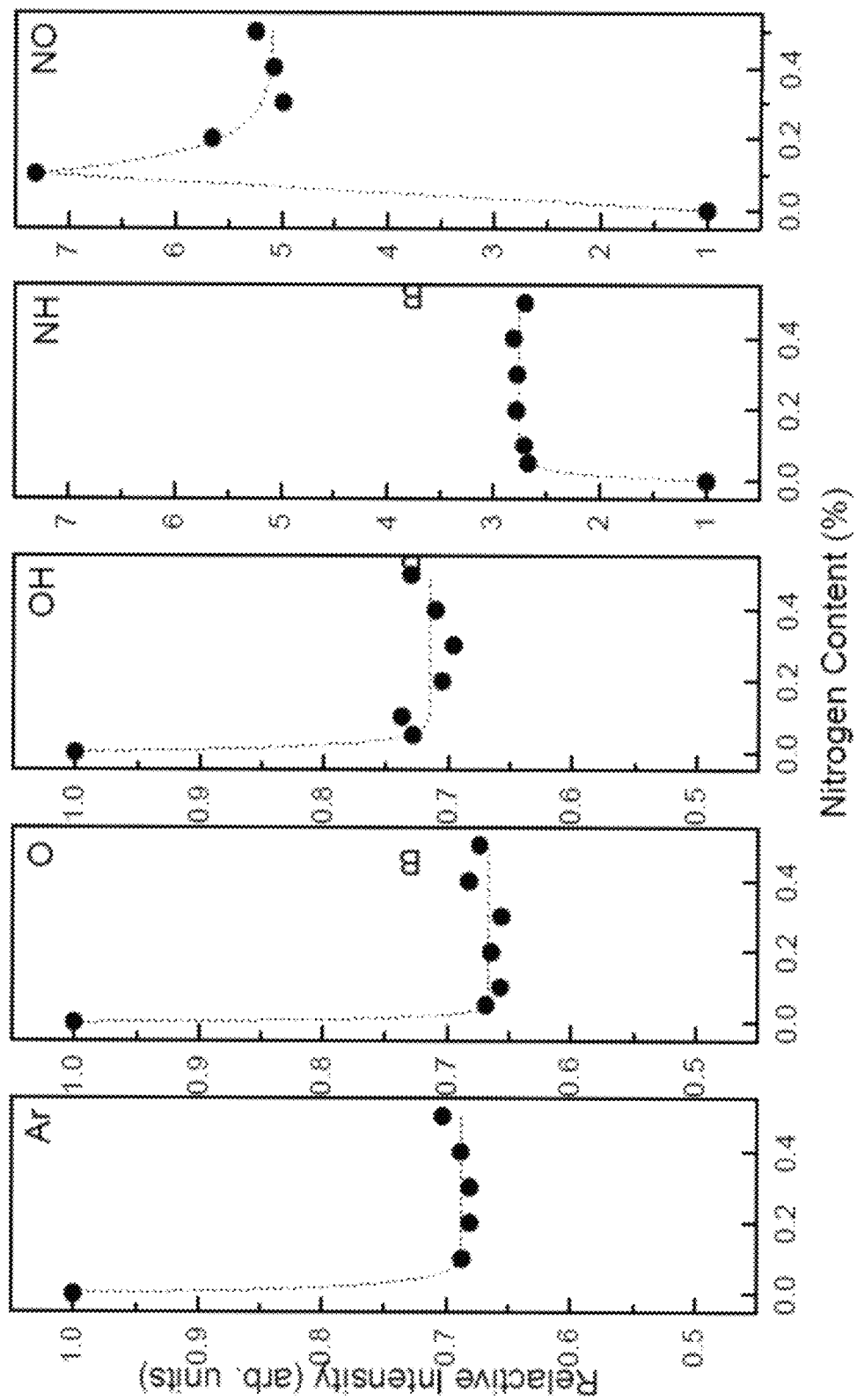
FIG. 6 is a schematic view showing the variation of the relative intensity of the major micro-plasma excited species relative to the addition ratio of nitrogen according to Example 2 of the present invention.

FIG. 5 shows the emission spectra of the major micro-plasma excited species at 190-550 and 550-1000 nm in the conditions of Example 1. FIG. 6 is a schematic view showing the variation of the relative intensity of the major micro-plasma excited species (Ar (750 nm), 0 (777 nm), OH (306 nm), NH (336 nm), and NO (236 nm)) relative to the addition ratio of nitrogen in the conditions of Example 1, wherein the addition ratio of nitrogen is 0-0.5%.

Figure 7A:
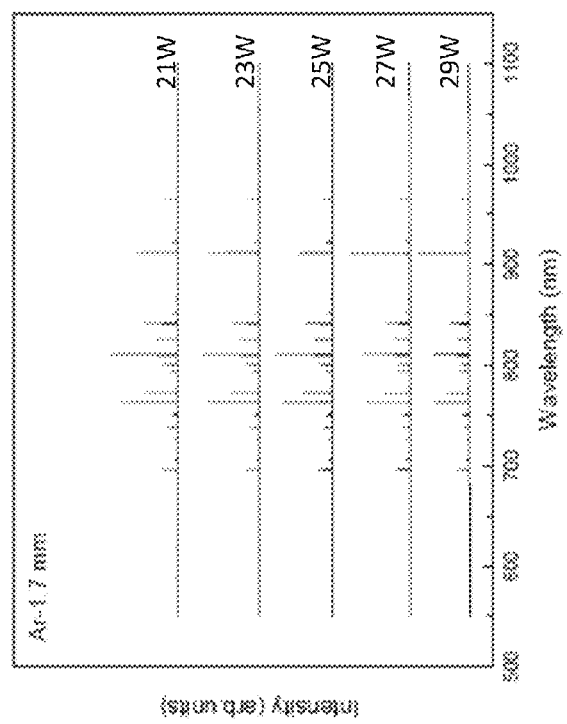
FIGS. 7(a) and 7(b) show the emission spectra of argon according to Example 2 of the present invention: (a) 1.7 mm; (b) 3.7 mm.
Figure 7A:
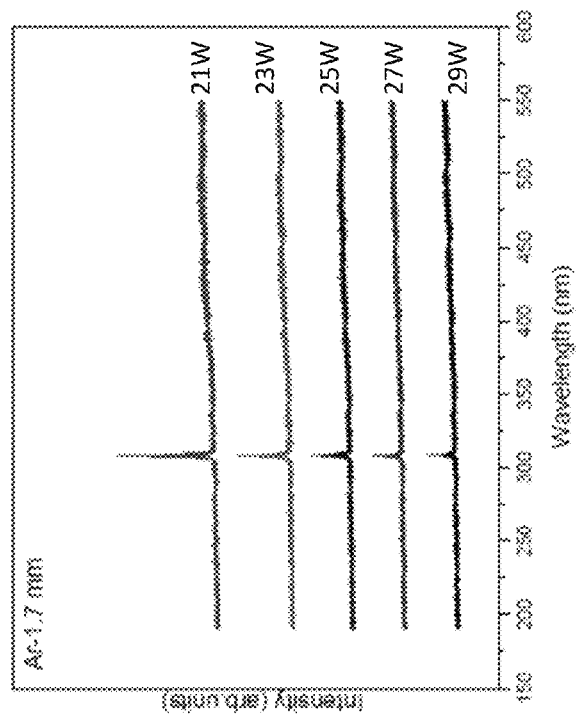
Figure 7B:
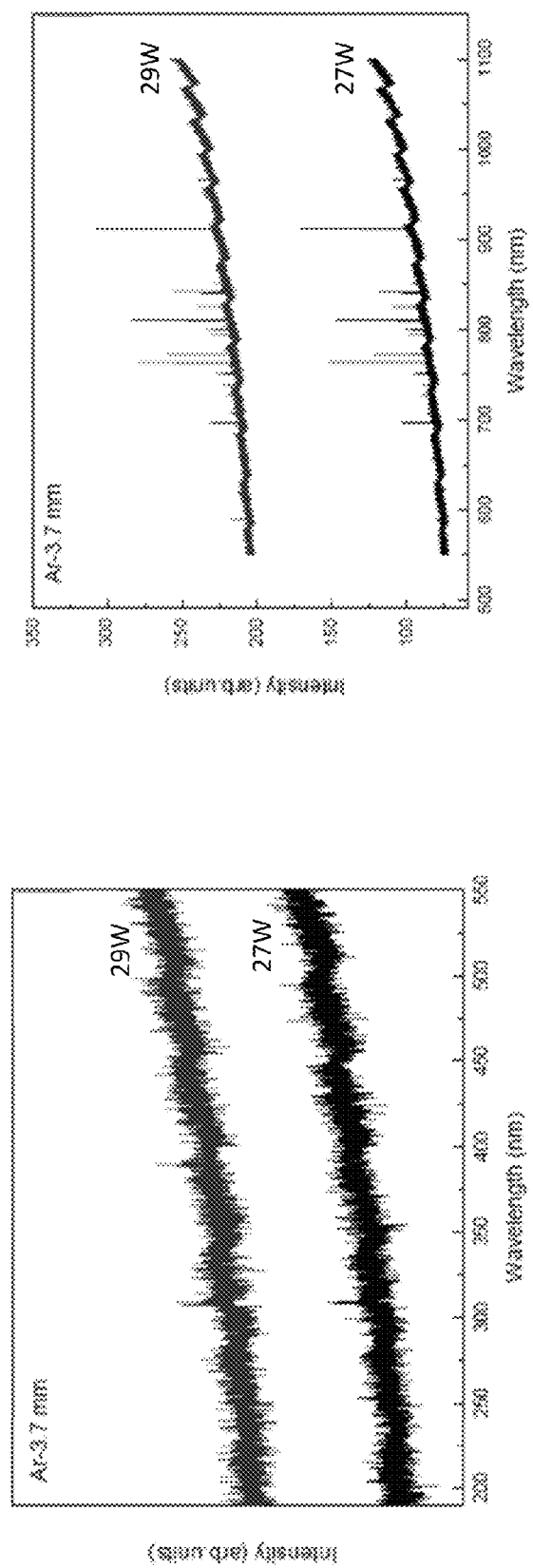
Figure 8A:
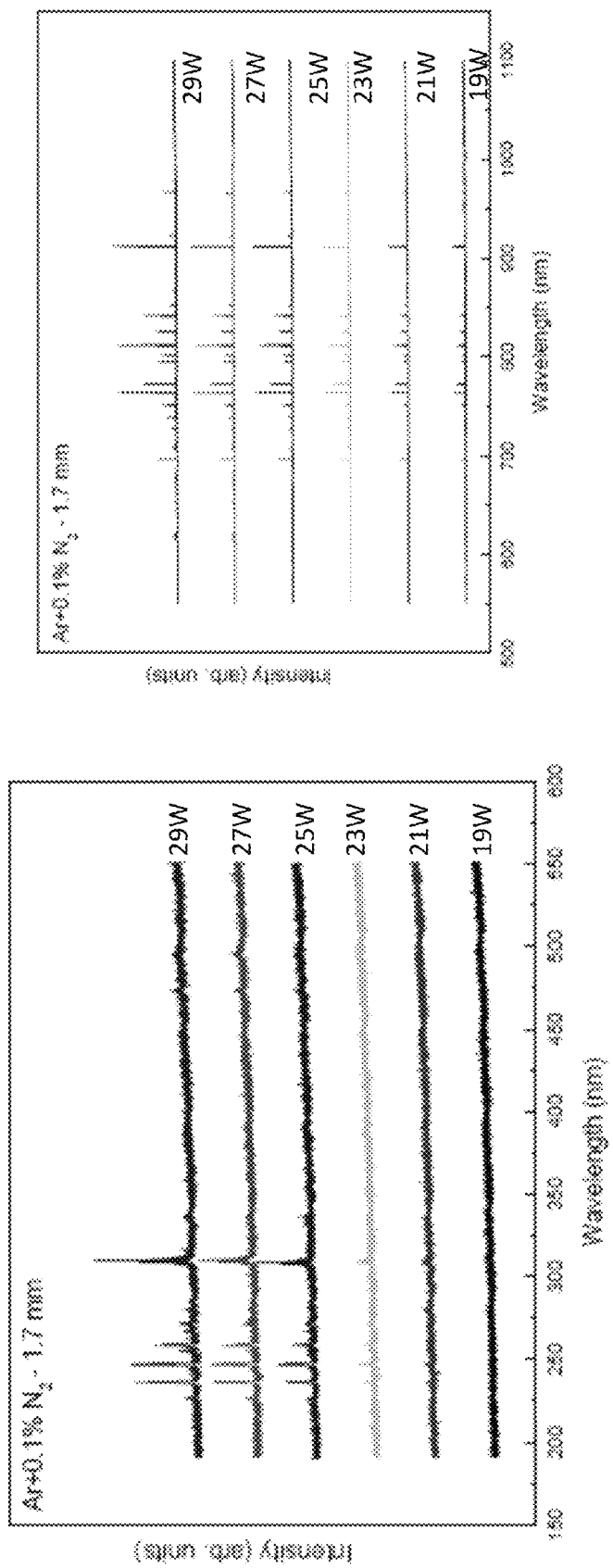
FIGS. 8(a) and 8(b) show the emission spectra of argon and nitrogen having an addition ratio of 0.1% according to Example 2 of the present invention: (a) 1.7 mm; (b) 3.7 mm.
Figure 8B:
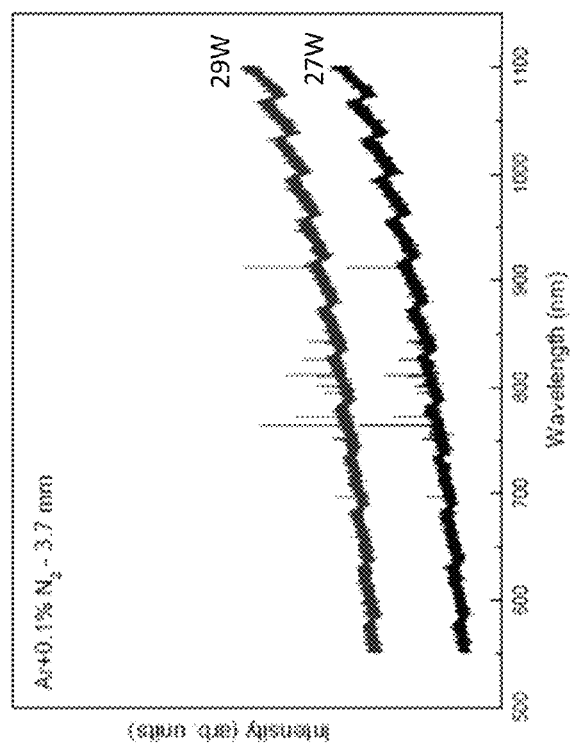
Figure 8B:
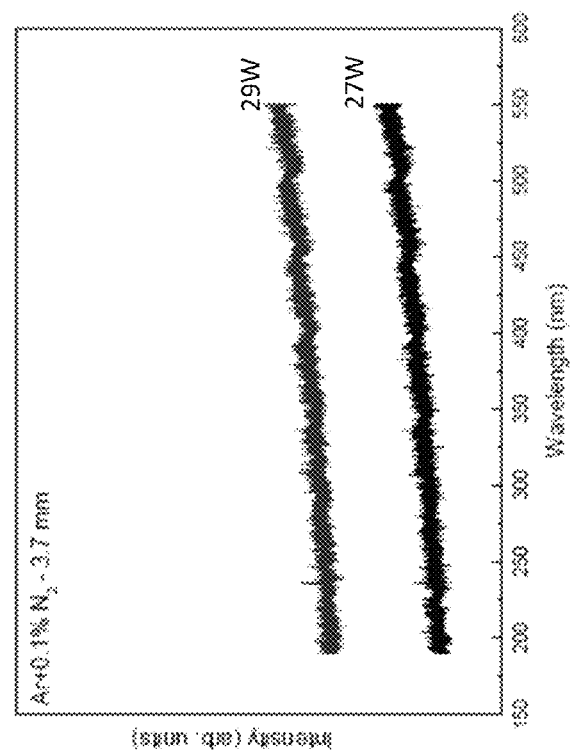
Figure 9A:
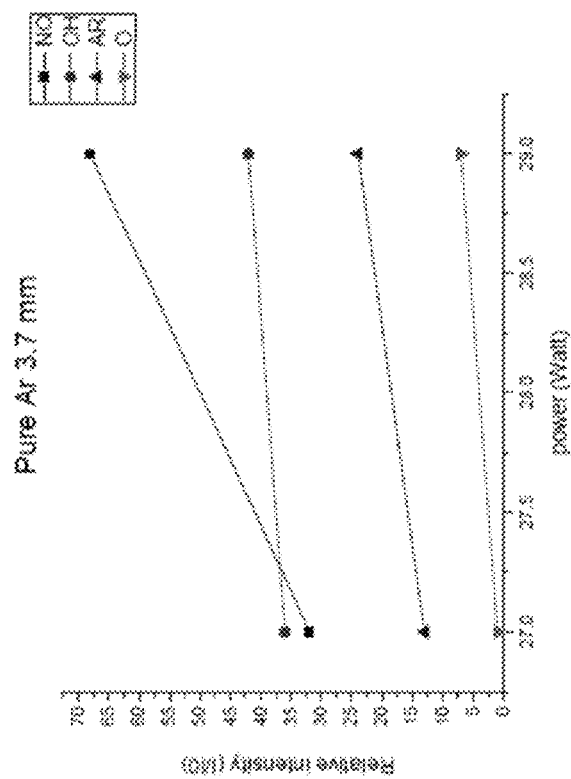
FIGS. 9 (a) and 9(b) are a schematic view showing the variation of the relative intensity of the produced micro-plasma excited species relative to the excitation power according to Example 2 of the present invention.
Figure 9A:
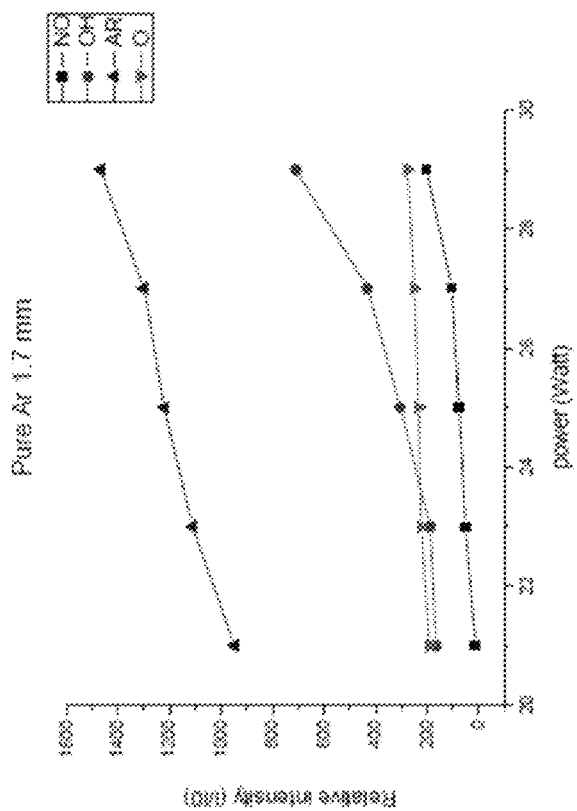
Figure 9B:
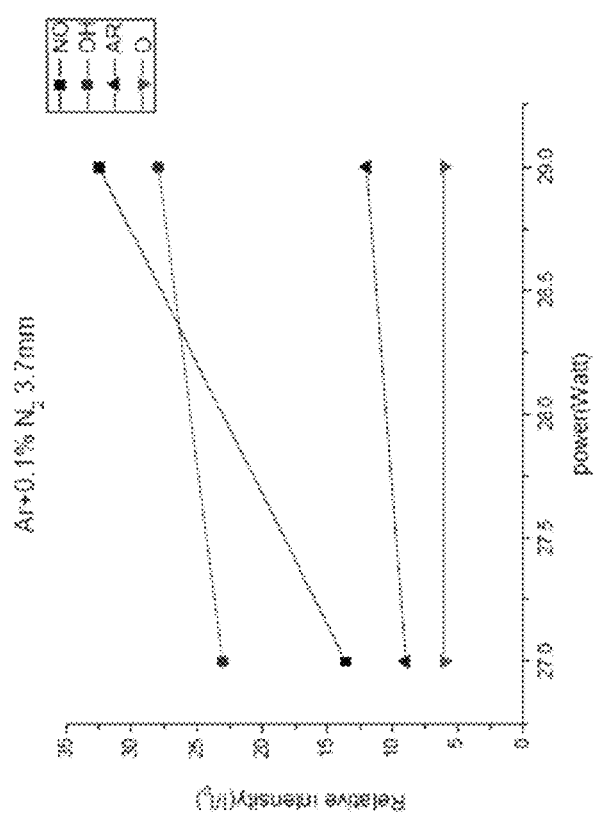
Figure 9B:
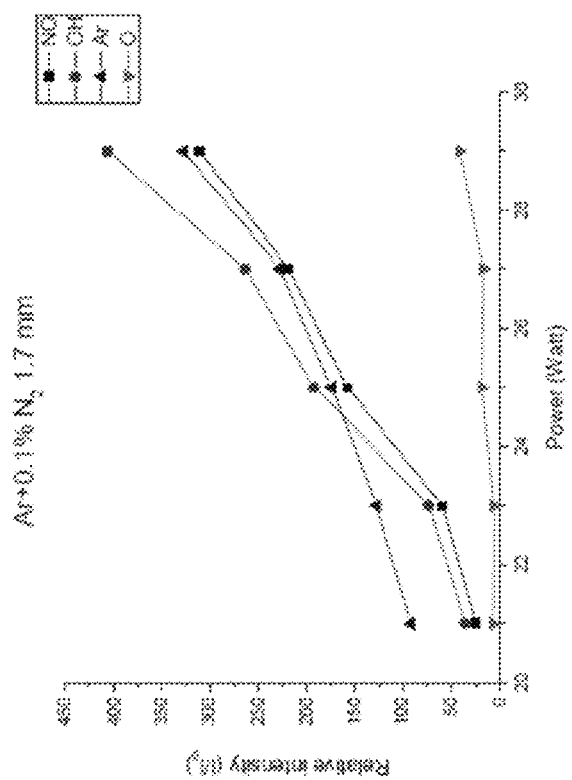

FIGS. 7(a) and 7(b) show the emission spectra of argon according to Example 2 of the present invention: (a) 1.7 mm; (b) 3.7 mm. FIGS. 8(a) and 8(b) show the emission spectra of argon and nitrogen having an addition ratio of 0.1% according to Example 2 of the present invention: (a) 1.7 mm; (b) 3.7 mm. FIGS. 9(a) and 9(b) are a schematic view showing the variation of the relative intensity of the produced micro-plasma excited species (NO, OH, Ar, and O) relative to the excitation power in the conditions of Example 1, wherein (a) is under pure argon, and (b) is under argon with 0.1% nitrogen. From the results of FIG. 3 to FIG. 9, it can be confirmed that the produced micro-plasma of the present invention is adjustable for its composition and is low energy consumption.

The results of the above Examples 1 and 2 demonstrate the variation of the micro-plasma excited species relative to the different second gases, and thus the wavelength of emission light and the micro-plasma excited species produced in the micro-plasma may be known accordingly. Furthermore, the results of the above Examples 1 and 2 indicate that the generation of the micro-plasma excited species can be controlled by adding a small amount of the second gas.

Example 3

In Example 3, all conditions were substantially the same as in Example 1, except that the excitation power was 19, 21, 23, 25, 27, 29, and 31, and a temperature measurement system 5 was further included. With an excitation power of 19, 21, 23, 25, 27, 29, and 31, the temperatures produced by the micro-plasma were measured under a working distance of 3 mm, 6 mm, and 9 mm, respectively, and the results are shown in Table 1.

TABLE 1

| excitation power | working distance | | |
| --- | --- | --- | --- |
| | 3 mm | 6 mm | 9 mm |
| 19 | 36.4 ± 4.2 | 34 ± 3.8 | 32 ± 4.6 |
| 21 | 39.7 ± 3.7 | 37.3 ± 2.7 | 35.4 ± 2.8 |

TABLE 1-continued

| excitation power | working distance | | |
| --- | --- | --- | --- |
| | 3 mm | 6 mm | 9 mm |
| 23 | 41.8 ± 4.5 | 39.2 ± 2.4 | 38.3 ± 3.9 |
| 25 | 46.5 ± 3.4 | 45.4 ± 2.7 | 42.6 ± 2.6 |
| 27 | 48.8 ± 3.5 | 46.6 ± 3.2 | 45.4 ± 4.1 |
| 29 | 52.6 ± 2.8 | 52.0 ± 3.9 | 49.4 ± 4.1 |
| 31 | 54.9 ± 3.1 | 53.6 ± 4.3 | 51.2 ± 3.4 |
| 33 | 57.2 ± 3.3 | 55.9 ± 3.6 | 55.0 ± 2.6 |

The units of temperature is centigrade temperature (° C.), and the unit of applied power is Watt.

Figure 10:
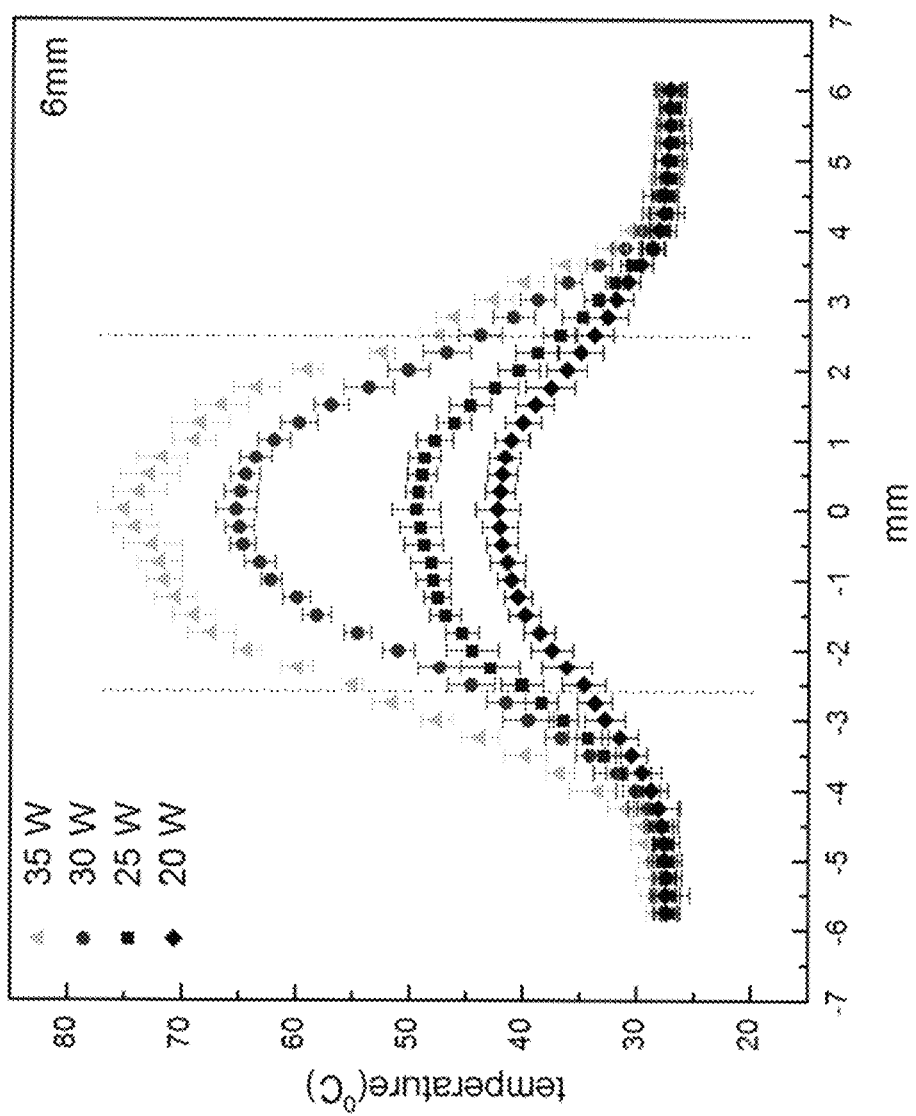
FIG. 10 shows temperature distributions of different parameters measured by the temperature measurement system according to Example 3 of the present invention.

The temperature parameters suitable for the human body may be chosen according to the measured result of Example 3. The variation in temperature is controlled by the power, the working distance, and the gases added. FIG. 10 shows temperature distributions of different parameters measured by the temperature measurement system.

Example 4

In Example 4, all conditions were substantially the same as in Example 1, except that the second gas was 0.5% of nitrogen, the excitation power was 17 W, the working distance was 9 mm, and the processing time of the micro-plasma was 5 to 15 seconds. In Example 4, the excited micro-plasma was applied on fibroblasts.

Comparative Example 1

In Comparative Example 1, the fibroblast was not treated by the excited micro-plasma, different from the fibroblast in Example 4.

Figure 11A:
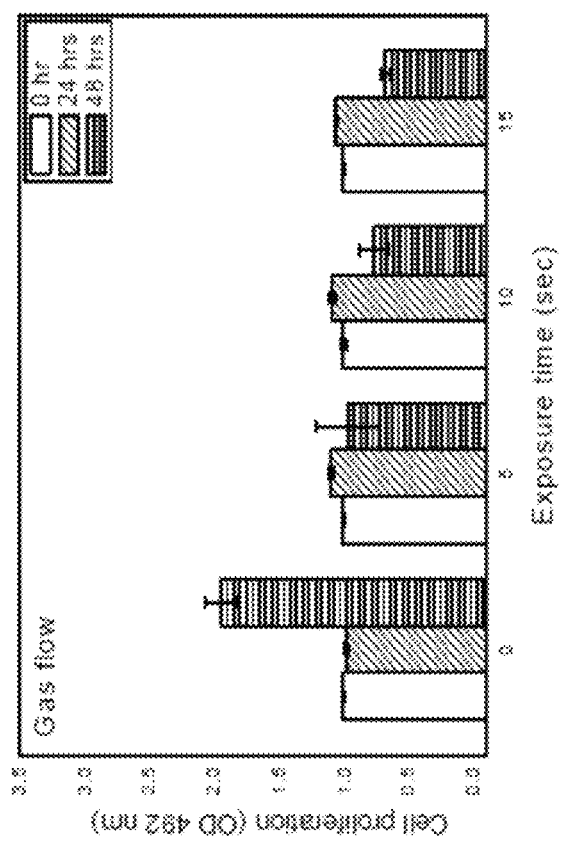
FIGS. 11 (a) to (d) show the schematic views of the proliferation of fibroblast L929 excited by the micro-plasma of nitrogen and argon according to Example 4 of the present invention.
Figure 11B:
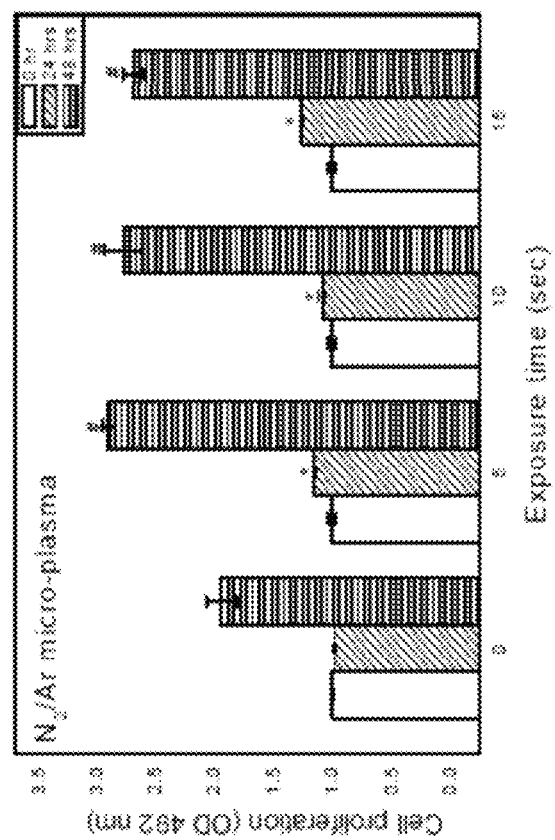
Figure 11D:
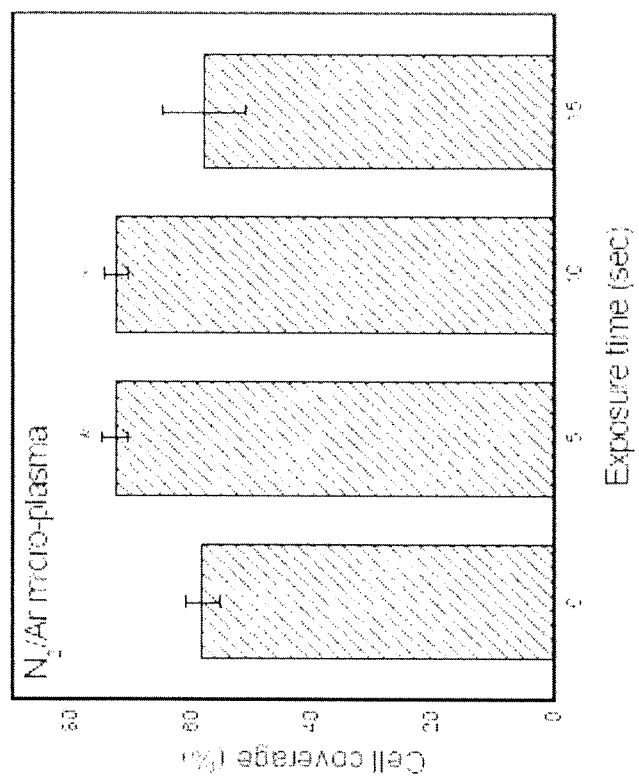
Figure 11C:
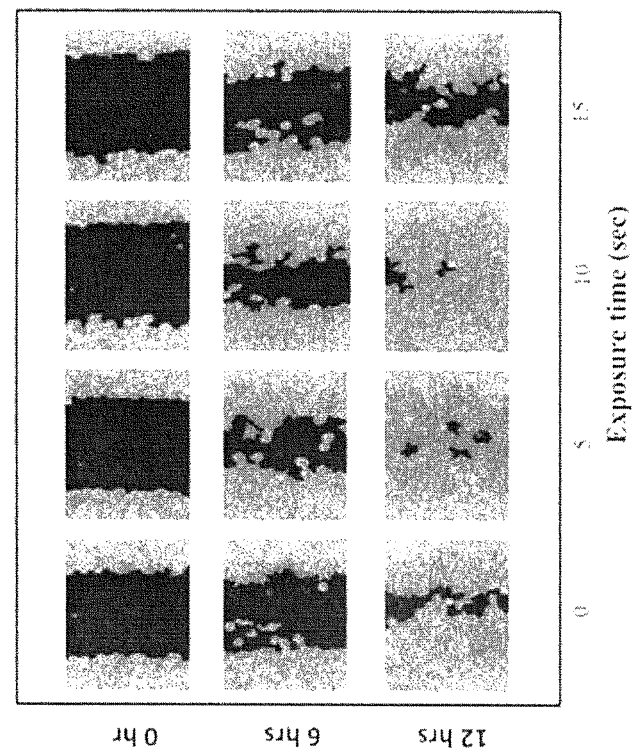

In FIGS. 11(a) and (b), the fibroblast L929 cells were proliferated by treatment of the micro-plasma of nitrogen and argon: (a) L929 cells were excited by the micro-plasma of nitrogen and argon at 5th, 10th, or 15th seconds, and the proliferation of the excited L929 was compared to the non-treated L929 cells of Comparative Example 1, and the cell number significantly increased almost 3 times at 48 hours as compared to 0 hour; (b) on the contrary, there was no significant change in the cell number of the fibroblast L929 in gas flow treatment. In FIGS. 11(c) and (d), the migration of the fibroblast L929 cells were stimulated by treatment of the micro-plasma of nitrogen and argon: (c) after 6 and 12 hours, the cells were excited by the micro-plasma of nitrogen and argon, and the representative images showing the progression of cell migration were taken; (d) there was a significant increase in the number of the fibroblast L929 cells by exposing to the micro-plasma of nitrogen and argon at 5, 10 or 15 seconds compared with that of Comparative Example 1 after 6 hours.

Example 5

In Example 5, normal and healthy C57BL/6 male mice were used for the following steps: the mice's back was barbered and a wound was created on the mice's back through a laser (the laser energy parameters were listed in Table 2) after the mice was given general anesthesia; and then the mice was given a micro-plasma treatment immediately after the wound was formed, wherein the treatment conditions were one minute each time per day for one day; one wounded mice was raised in a cage alone and given with sufficient food and drinking water in daily care. The rearing conditions complied with the provisions of institutional animal care and use, National Cheng Kung University (NCKU IACUC).

The excitation power of Example 5 was between 25 to 35 W. At first, the micro-plasma was excited by 5 slm of pure argon, and then after 10-15 seconds as the micro-plasma was stable, 0.1% of pure nitrogen was mixed therein at a power of 17 W to 25 W with a working distance of 3.7 mm, and the processing time of the micro-plasma was one minute each time per day.

Example 6

In Example 6, normal and healthy C57BL/6 male mice were used for the experiment, and all steps were substantially the same as in Example 5 except that the treatment conditions were one minute each time per day for three days. Further, the parameters of the micro-plasma of were the same as in Example 5.

Comparative Example 2

Normal and healthy C57BL/6 male mice were used for the experiment. The mice's back was barbered and a wound was created on the mice's back through a laser (the laser energy parameters were listed in Table 2) after the mice was given general anesthesia, but the wound was not treated by the micro-plasma.

TABLE 2

| laser type | RF $CO_2$ LASER, ALL Metal Sealed Type |
|---|---|
| peak power | 13 W (13 J/sec) |
| laser mode | TEMoo (10.6 μm) |
| pulse duration | 3000 μs, 39 mJ |
| repetition | 1 sec/single, 3 cycles |
| Overlap (degree) | $3^{th}$ |
| distance | 0.3 mm |
| wound area | 3 * 20 mm |
| pixel size | ≥100 mm |
| cooling | air cooling |

Figure 12A:
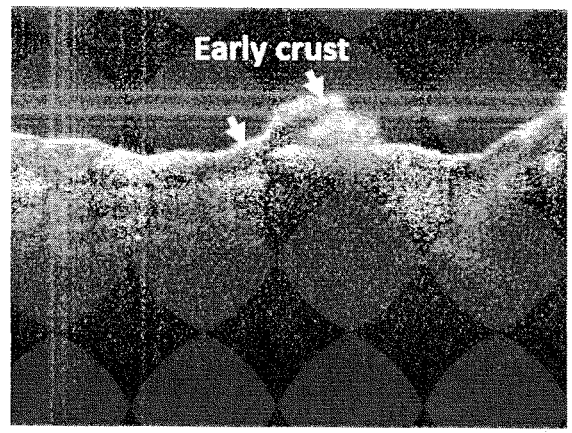
FIGS. 12 (a), (c) and (e) are backscattered intensity OCT images, and FIGS. 12 (b), (d) and (f) are histological images.
Figure 12B:
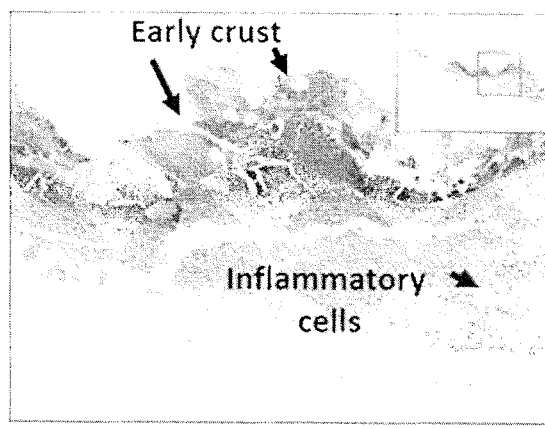
Figure 12C:
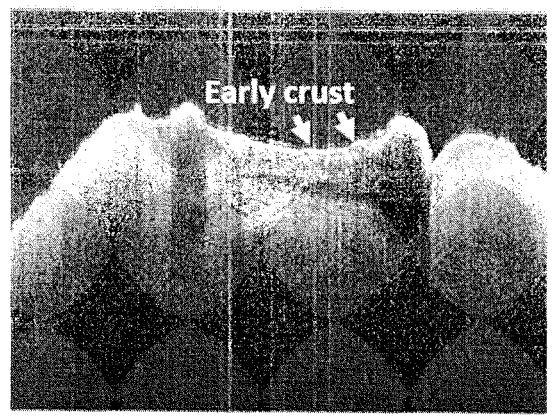
Figure 12D:
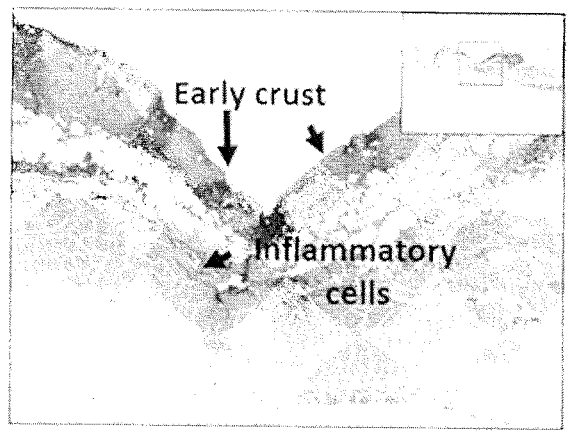
Figure 12E:
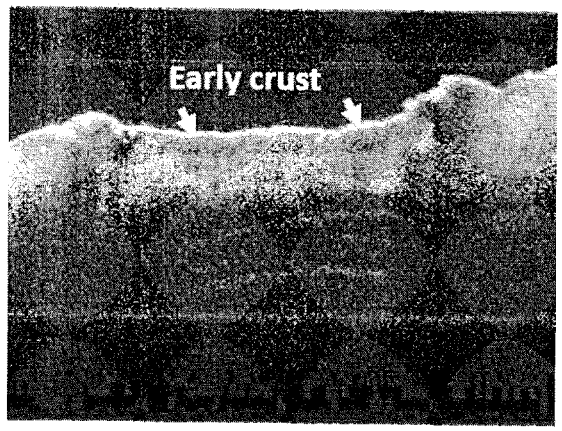
Figure 12F:
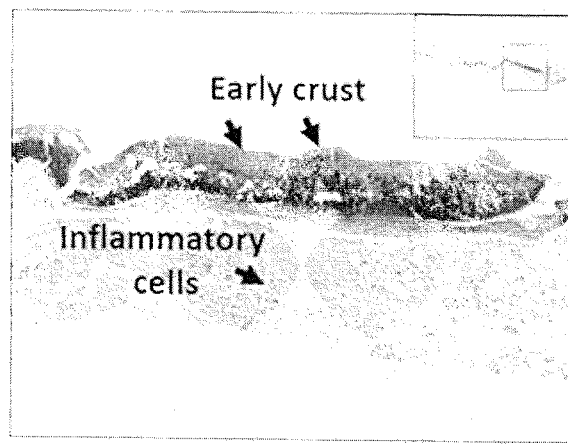
Figure 13A:
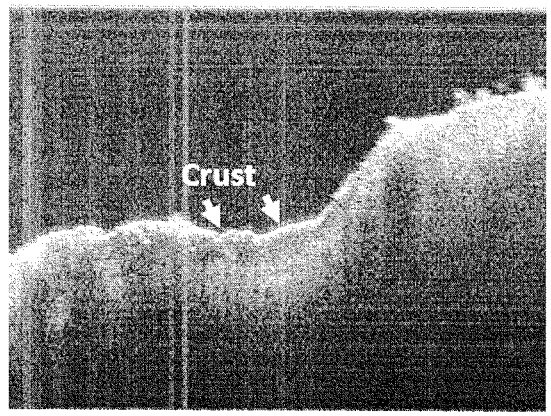
FIGS. 13 (a), (c) and (e) are backscattered intensity OCT images, and FIGS. 13 (b), (d) and (f) are histological images.
Figure 13B:
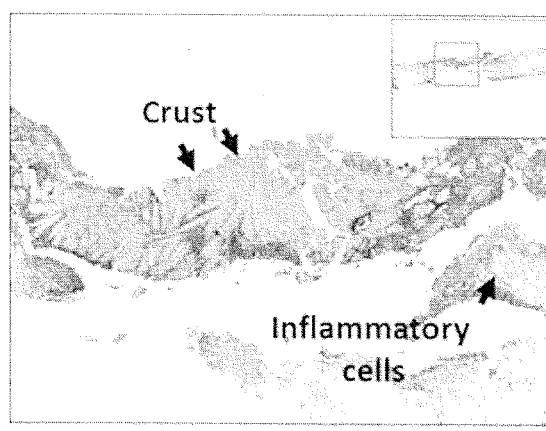
Figure 13C:
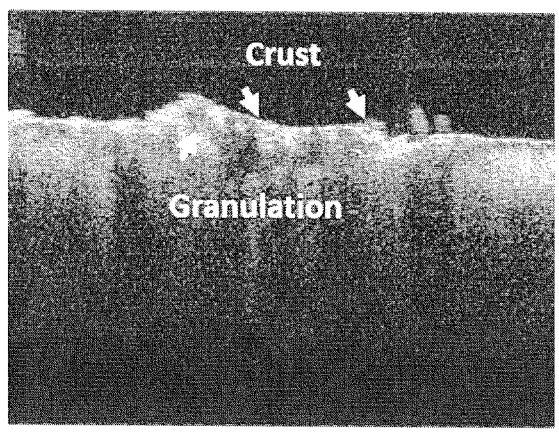
Figure 13D:
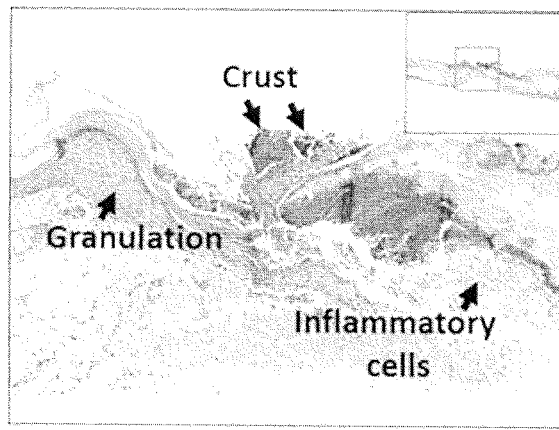
Figure 13E:
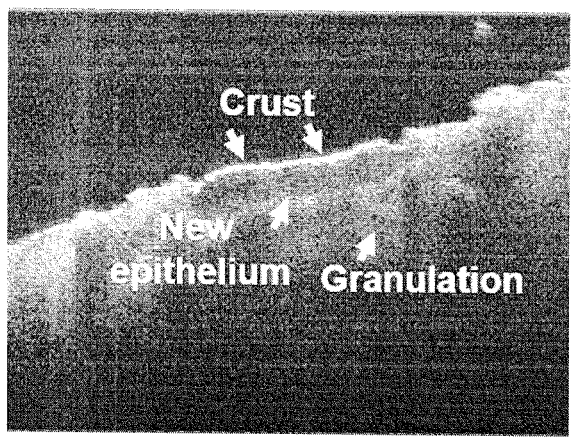
Figure 13F:
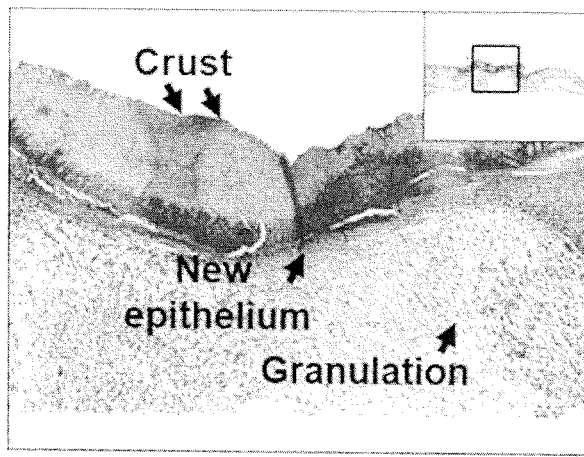

FIGS. 12(a), (c), and (e) are backscattered intensity OCT images, and FIGS. 12(b), (d), and (f) are histological images. FIGS. 12 (a) and (b) are images of the wound caused by laser; FIGS. 12 (c) and (d) are images of the wound caused by the treatment with micro-plasma one time. FIGS. 12 (e) and (f) images of the wound caused by the treatment with micro-plasma three times and observed for three days.

FIGS. 13 (a), (c), and (e) are backscattered intensity OCT images; FIGS. 13 (b), (d), and (f) are histological images. FIGS. 13(a) and (b) are images of the wound caused by laser; FIGS. 13 (c) and (d) are images of the wound caused by the treatment with micro-plasma one time. FIGS. 13 (e) and (f) are images of the wound caused by the treatment with micro-plasma three times and observed for seven days.

The results of Examples 5 and 6 indicated that the micro-plasma produced according to the present invention has biocompatibility for the use for the wound treatment and histiocyte.

Although the present invention has been explained in relation to its preferred embodiment, it is to be understood that many other possible modifications and variations can be made without departing from the spirit and scope of the invention as hereinafter claimed.

The micro-plasma of the present invention is well suited for wound repair, and a moderate micro-plasma system close to the temperature of human body is used to assist and treat sensitive wounds after laser treatment, thereby shortening the recovery time required for recovery to the optimum state after laser surgery. It is helpful for the modern people who are engaged in busy work but desire to improve skin problems effectively and quickly, and for the people who have aging skin and look forward to young looking. The present invention achieves the objects that patients feel painless and complete the steps of wound care comfortably and quickly after receiving micro-plasma therapy. Therefore, the present invention satisfies industrial applicability.

What is claimed is:

1. A method for wound treatment, comprising the following steps:
   (A) providing a device comprising a first gas storage unit, a second gas storage unit, a micro-plasma generation unit, a power supply unit, and a temperature measurement system for measuring an average temperature of the micro-plasma, which is within a range of 34-40° C.;
   (B) introducing helium or argon stored in the first gas storage unit into the micro-plasma generation unit to excite a micro-plasma to a steady state within a predetermined time;
   (C) introducing oxygen or nitrogen stored in the second gas storage unit into the micro-plasma generation unit so as to produce a micro-plasma containing micro-plasma excited species; and
   (D) contacting the wound with the micro-plasma excited species;
   wherein an addition ratio of the nitrogen is within a range of 0.1-2% and an addition ratio of the oxygen is within a range of 0.1-5%; and
   wherein the excitation power used for producing the micro-plasma is within a range of 1-30 W.

2. The method of claim 1, wherein the micro-plasma generation unit of the step (A) comprises a capillary tube in which the micro-plasma is excited to produce a low temperature micro-plasma.

3. The method of claim 1, wherein the first gas storage unit of the step (A) further comprises a gas flow monitor for showing the steady state of the excited micro-plasma.

4. The method of claim 1, wherein a flow rate of helium or argon is 1-10 Standard Liters per Minute (SLM).

5. The method of claim 4, wherein the flow rate of helium or argon is within a range of 1-5 SLM.

6. The method of claim 1, wherein the addition ratio of the oxygen is within a range of 0.1-2%.

7. The method of claim 1, wherein the addition ratio of the nitrogen is within a range of 0.1-1%.

8. The method of claim 1, wherein a processing time of the micro-plasma is within a range of 5-300 seconds.

9. The method of claim 1, wherein the excitation power is within a range of 15-25 W.

10. The method of claim 1, wherein the device of the step (A) further comprises a micro-plasma emission spectrometer for quantitatively or qualitatively detecting a type of the micro-plasma excited species.

11. The method of claim 1, wherein the micro-plasma excited species is reactive oxygen species (ROS) or reactive nitrogen species (RNS).

12. The method of claim 1, wherein contacting the wound is performed in a subject in need thereof.

13. The method of claim 12, wherein the subject is a human.

14. The method of claim 12, wherein the step (C) further comprises setting a working distance between the subject and the micro-plasma generation unit.

15. The method of making claim 14, wherein the working distance is within a range of 1-12 mm.

* * * * *